United States Patent [19]

Eibofner et al.

[11] Patent Number: 4,486,174
[45] Date of Patent: Dec. 4, 1984

[54] ARRANGEMENT FOR DISPENSING OF MAINTENANCE MEDIA TO MEDICAL, PARTICULARLY DENTAL, HANDPIECES

[75] Inventors: Eugen Eibofner, Biberach; Ernst Strohmaier, Bd. Schussenried, both of Fed. Rep. of Germany

[73] Assignee: Kaltenbach & Voight GmbH & Co., Biberach an der Riss, Fed. Rep. of Germany

[21] Appl. No.: 341,089

[22] Filed: Jan. 20, 1982

[30] Foreign Application Priority Data

Feb. 6, 1981 [DE] Fed. Rep. of Germany ....... 3104237

[51] Int. Cl.$^3$ ............................ A61C 1/02; A61C 1/08
[52] U.S. Cl. ...................................... 433/104; 433/98
[58] Field of Search ...................... 433/104, 98, 84, 27, 433/99, 101; 184/6.3

[56] References Cited

U.S. PATENT DOCUMENTS

| | | | |
|---|---|---|---|
| 2,532,054 | 11/1950 | Broussard et al. | 433/84 |
| 2,855,672 | 10/1958 | Franwick et al. | 433/84 |
| 3,106,021 | 10/1963 | Borden | 433/104 |
| 3,129,511 | 4/1964 | Williams | 433/104 |
| 3,210,846 | 10/1965 | Balkin | 433/98 |
| 3,556,669 | 1/1971 | Valeska et al. | 433/104 |
| 3,963,391 | 6/1976 | Thorburn et al. | 433/104 |

FOREIGN PATENT DOCUMENTS 2267739 11/1975 Fed. Rep. of Germany ...... 433/104

Primary Examiner—John J. Wilson
Attorney, Agent, or Firm—Scully, Scott, Murphy & Presser

[57] ABSTRACT

An arrangement for the dispensing of cleaning and/or lubricating media, which can be placed under pressure in a receptacle, as maintenance media to movable elements containing medical, and particularly dental handpieces. The maintenance medium is forced by means of a pressure drive out of a dispensing orifice of the receptacle through an inlet opening of the handpiece which is attached to the receptacle at the dispensing orifice and whereby, during the forcing of the maintenance medium into the movable elements of the handpiece, they are placeable into motion through a motion drive. The maintenance medium can be formed by liquid cleaning and/or lubricating media, for instance, such as oil. The arrangement of a separate power source, for the motion drive and for the pressure drive, in a simple and economical manner facilitates the motion drive as well as the pressure drive to be supplied with the required energy in a completely targeted manner by the current power source for a secure operation, so that neither the forcing out of the maintenance medium nor the action of the motion drive on the movable components of the handpiece are adversely influenced in any manner or could even be inhibited.

1 Claim, 13 Drawing Figures

FIG.1

ARRANGEMENT FOR DISPENSING OF MAINTENANCE MEDIA TO MEDICAL, PARTICULARLY DENTAL, HANDPIECES

BACKGROUND OF THE INVENTION

1. Field of the Invention

The present invention relates to an arrangement for the dispensing of cleaning and/or lubricating media, which can be placed under pressure in a receptacle, as maintenance media to movable elements containing medical, and particularly dental handpieces. The maintenance medium is forced by means of a pressure drive out of a dispensing orifice of the receptacle through an inlet opening of the handpiece which is attached to the receptacle at the dispensing orifice and whereby, during the forcing of the maintenance medium into the movable elements of the handpiece these are placeable into motion through a motion drive. The maintenance medium can be formed by liquid cleaning and/or lubricating media, for instance, such as oil. For example, a maintenance medium can be utilized as is set forth in German Laid-open Patent application No. 29 16 552.

2. Discussion of the Prior Art

For the formation of the pressure drive, the receptacle containing the maintenance medium in such an arrangement can be placed under pressure, for example, pursuant to German Patent 561 205 through a hand air-blower, or in accordance with German Laid-open Patent Application No. 29 18 519 through a compressor or the like. The pressure drive can also be formed, pursuant to Swiss Pat. No. 535 575, through the internal pressure of a spray container which forms the receptacle and contains the maintenance medium and a drive medium. Finally, pursuant to the publication "Turboclean" of the company Scania Dental AB, the pressure drive can be formed, with the elimination of a separate receptacle containing the maintenance medium, through an air gun which dispenses compressed air through a mouthpiece, and which has its mouthpiece applied to the inlet opening of the handpiece which is previously filled with maintenance medium.

The arrangements which have become known from German Pat. No. 561 205, Swiss Pat. No. 535 575 and the publication "Turboclean", are subject to the common disadvantage in the lack of a motion drive for the movable components of the handpiece. Hereby, the moistening of particularly the movable handpiece components with the maintenance medium is incomplete or even rendered impossible, so that obtaining of the sought after maintenance effect is rendered doubtful.

For the formation of the motion drive which, for example, can be a reversing push-pull drive, for instance, for filing handpieces, or a rotary drive, for instance, for drilling or boring handpieces, in the case of a rotary drive in an arrangement of the above-mentioned type, the rotatable work tool drive shaft of the handpiece which is immersed in the receptacle containing the maintenance medium, pursuant to Swiss Pat. No. 259 955 can be set into rotation through a separate hand cam drive or, pursuant to the publication, "Kavo-Tauchöl-und Reinigungsbesteck 2140", of the company Kaltenbach & Voigt, through the already currently present operating rotary drive of the handpiece. Finally, the motion drive pursuant to German Laid-open Patent Application No. 29 18 510 can be formed by a motor drive which is associated with the receptacle containing the maintenance medium, which drives a rotary follower arranged within the receptacle, which upon application of the inlet opening of the handpiece to the dispensing opening of the receptacle, can be brought into engagement with the rotatable work tool drive shaft of the handpiece. The arrangements which have become known from Swiss Pat. No. 259 955 and the publication "Kavo-Tauchöl-und Reinigungsbesteck 2140" have the common disadvantage that, without considering a possibly relatively intensive moistening of particularly the movable handpiece components, the maintenance medium and the contaminants cannot be or at least not completely rinsed out of the handpiece, so that also in this instance there is rendered questionable the sought-after maintenance effect.

The motor drive which, in the arrangement pursuant to German Laid-open Patent Application No. 29 18 510 is provided as a rotary drive, for example, formed through a turbine wheel-like disk or an electromotor, should concurrently produce also the pressure drive; since in the case of a turbine wheel-like disk which is fixedly arranged on the shaft-like rotary follower, the pressurized drive air of the disk should flow past the latter, so as to force the maintenance medium downstream of the rotating disk out of the dispensing opening of the receptacle, whereas in the case of the electromotor there is provided, operating in conjunction with the shaft-like rotary follower by means of a threaded connection, a piston displaceable axially-parallel relative to the shaft which, for a rotating rotary follower, should force the maintenance medium downstream of the piston out of the dispensing orifice of the receptacle. Thus, for the rotary drive, in effect the motion drive, as well as for the pressure drive, there is thus provided a common power source, in essence, the motor drive which is supplied with compressed air or electric current. This has the result that, for example, in the case of the turbine wheel-like disk, there is required such a high use of air and in the case of the electromotor such a high use of current is required in order to set the disk or, respectively the motor into rotation and to concurrently force out the maintenance medium, that the operation of the known arrangement becomes uneconomical. Independently thereof, the pressure drive, in effect the forcing out of the maintenance medium, as well as the motion drive, in effect the rotation of the drive shaft of the handpiece, can be fully depleted since in the case of the disk there exists the danger that upstream of the disk, due to the small interspace between the disk rim and the receptacle wall, there will be produced too high a back pressure, whereas in the case of the electromotor there exists the danger that the threaded connection will bind between the piston and the shaft-like rotary follower. Finally, for the known arrangement, in the case of the turbine wheel-like disk, there is present the further danger that, in particular, hereby the rotary drive also will be rendered ineffective since the receptacle is provided with an exhaust air outlet opening only upstream of the disk but not downstream of the disk.

SUMMARY OF THE INVENTION

The present invention thus contemplates the provision of an arrangement of the above-mentioned type which, while affording a highly efficient maintenance and economical operation, will safely prevent any exhaustion of the pressure drive as well as of the motion drive.

The advantages which are achieved by means of the present invention can be essentially contemplated in that, due to the arrangement of a separate power source, for the motion drive and for the pressure drive, in a simple and economical manner the motion drive as well as the pressure drive can be supplied with the required energy in a completely targeted manner by the current power source for a secure operation, so that neither the forcing out of the maintenance medium nor the action of the motion drive on the movable components of the handpiece are adversely influenced in any manner or could even be inhibited.

BRIEF DESCRIPTION OF THE DRAWINGS

Reference may now be had to the following detailed description of exemplary embodiments of the invention, taken in conjunction with the accompanying drawings; in which.

DETAILED DESCRIPTION

Figure 1:
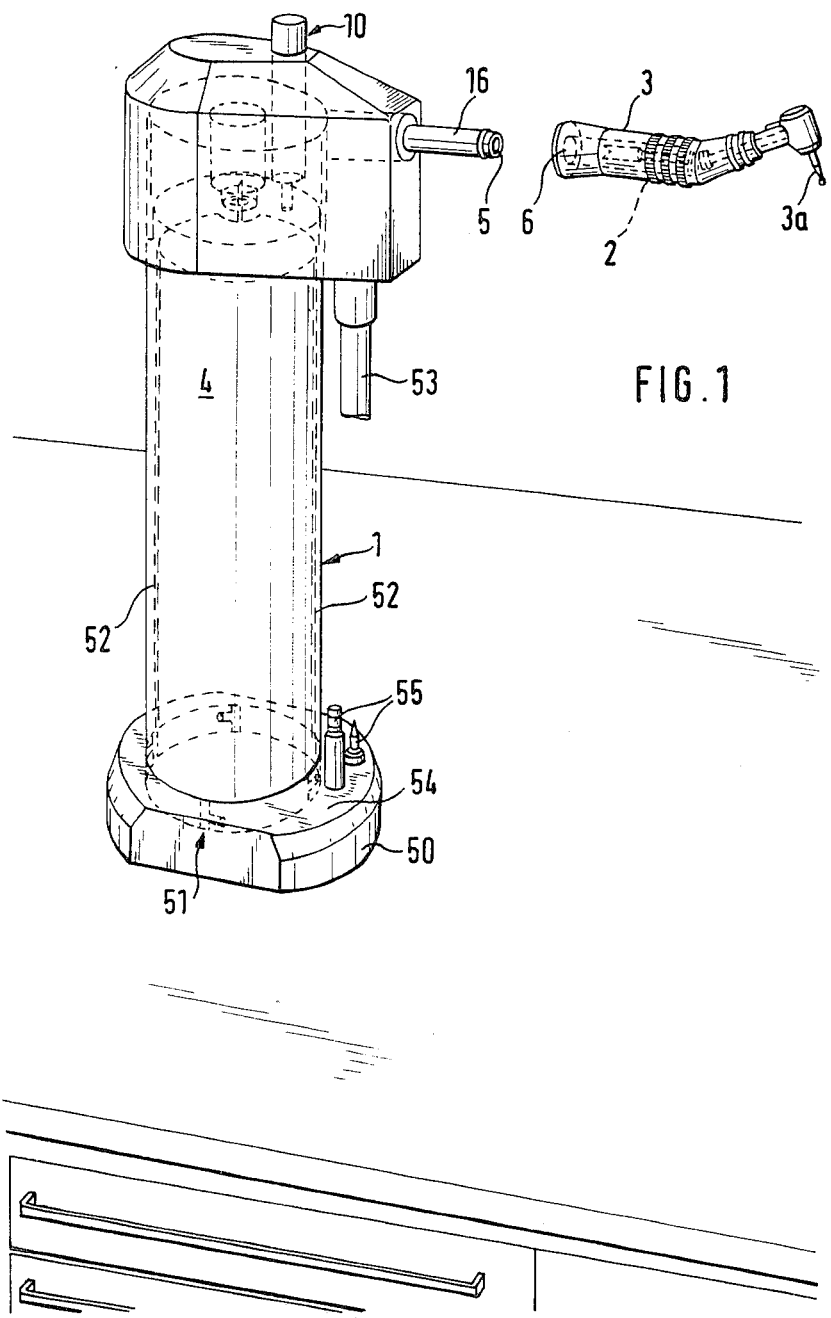
FIG. 1 illustrates a perspective view of an arrangement for the dispensing of maintenance media with the dental handpiece shown closely ahead of the dispensing opening of the maintenance medium receptacle.
Figure 2:
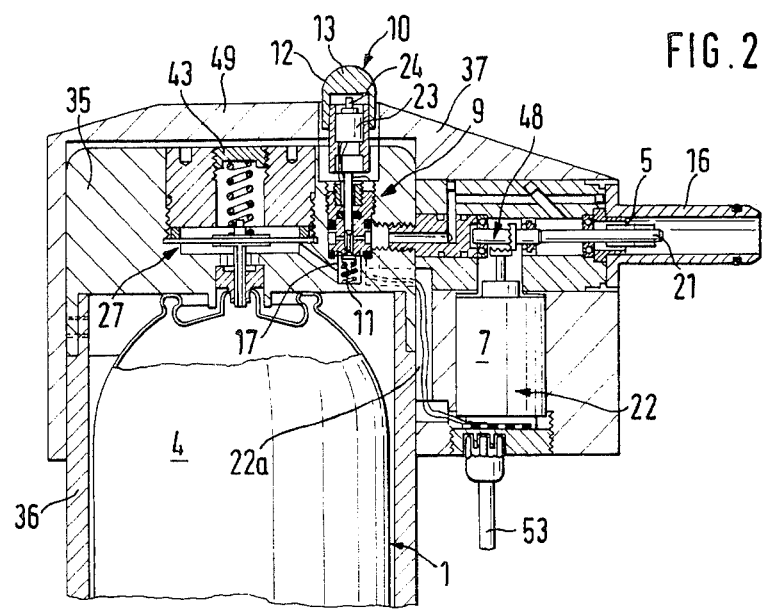
FIG. 2 illustrates a section through the upper portion of the arrangement with receptacle for maintenance media formed by a spray container taken along line II—II in FIG. 3.
Figure 3:
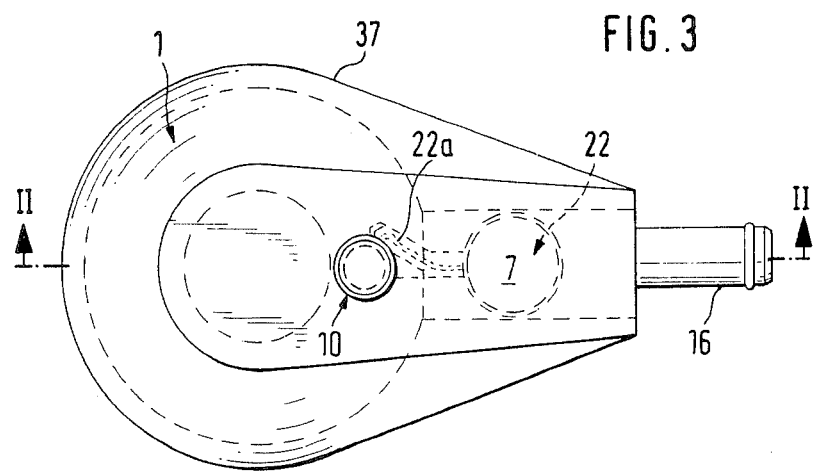
FIG. 3 is a top plan view of the arrangement according to FIG. 2.
Figure 4:
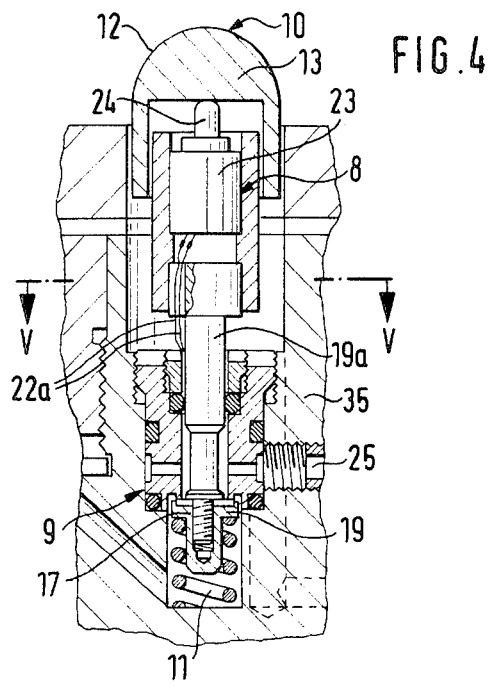
FIG. 4 is a detail on an enlarged scale of the arrangement illustrated in FIG. 2.
Figure 5:
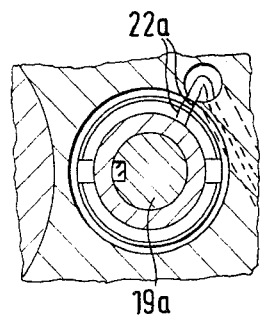
FIG. 5 is a section taken along line V—V in FIG. 4.

The arrangement for the dispensing of maintenance media consists of a receptacle 1 in which there is contained the maintenance medium, and which is placeable under pressure or which stands under pressure when the receptacle 1 consists of a spray container, for instance, a spray can. The dispensing of the maintenance medium from the receptacle 1 is conducted to movable components 2 containing the handpieces 3. The movable components 2, for example, can be a reciprocating pusher for a saw or a file inserted as a work tool into the handpiece 3, or pursuant to FIG. 1, a rotatable drive shaft for a drill, borer or the like inserted as the work tool 3a. The maintenance medium is forced out by means of a pressure drive 4 from a dispensing opening 5 of the receptacle 1 through an inlet opening 6 of the handpiece 3 into the latter. During this forcing in of the maintenance medium, the components 2 of the handpiece 3 can be set in motion by means of a motion drive 7. The pressure drive 4, in lieu of the internal pressure of a spray container, can basically be also formed by a cylinder-piston arrangement (not shown), for example, a compressor, which is associated with the receptacle 1.

As illustrated in the drawing, the motion drive 7 and the pressure drive 4 each have associated therewith a separate power source and, in effect, as elucidated hereinbelow, the motion drive 7 has electrical current provided for an electromotor, and the pressure drive 4 has pressurized gas provided in the receptacle 1, for example, air, nitrogen, freon, propane-butane or the like. The two power sources need, however, not be of different types, for example, the motion drive 7 in lieu of the electrical current can also have compressed air associated therewith, when an air motor or the like is utilized, with the prerequisite that the power sources which coincide this instance, as mentioned, are presently separately associated with the two drives 4 and 7.

Thus, the motion drive power source, as well as the pressure drive source, are each adapted to be placed into and out of operation through a separate switch element 8 or 9. The two switch elements 8 and 9, however, have a common actuating element 10 associated therewith. Through this single actuating element 10, although there two separate power sources and two separate circuit elements are present, there can be achieved the simple operation of the arrangement.

Basically, the two separate power sources can be concurrently placed into operation. However, it is advantageous that initially the motion drive power source and thereafter the pressure drive power source can be set into operation, inasmuch as the maintenance medium will then be conducted to the already moving movable components 2, and the last-mentioned are more intensively moistened in this manner with the maintenance medium.

The common actuating element 10 is hereby formed by a pressure element 12 which, in opposition to the action of a spring 11, is adapted to move the two switch elements 8, 9 into a switch position corresponding to one of the operating conditions of the two power sources.

Figure 7:
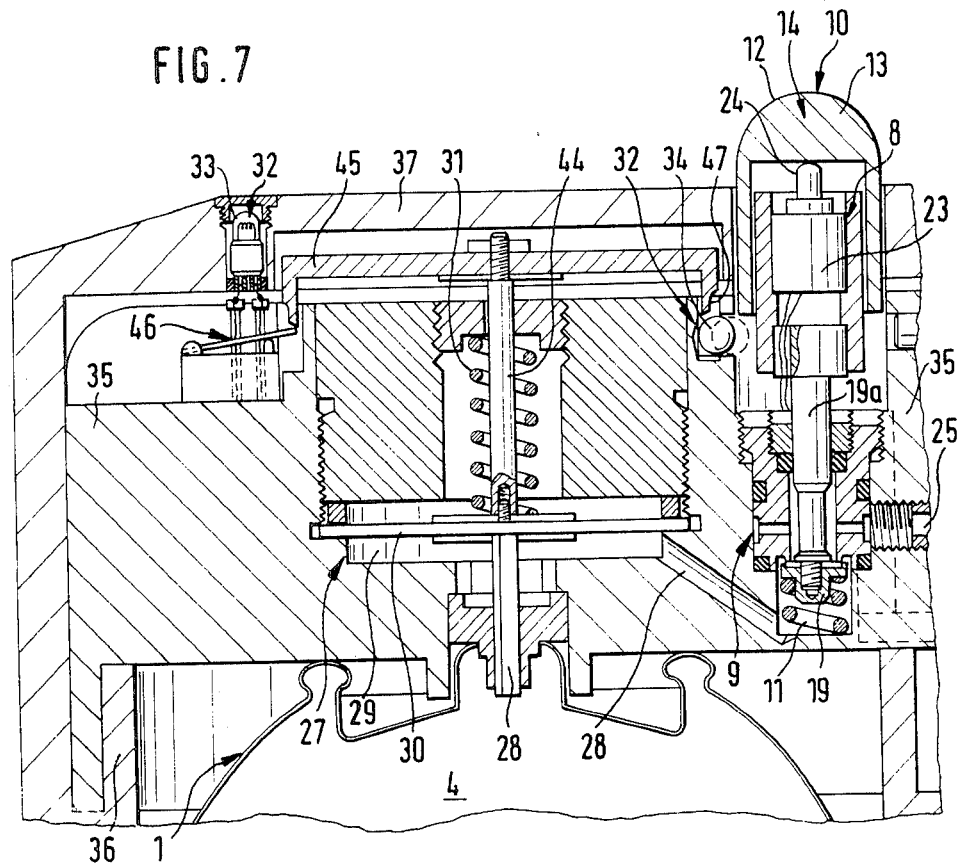
FIG. 7 is a modified embodiment in comparison with that of FIG. 2 shown in an enlarged scale.
Figure 8:
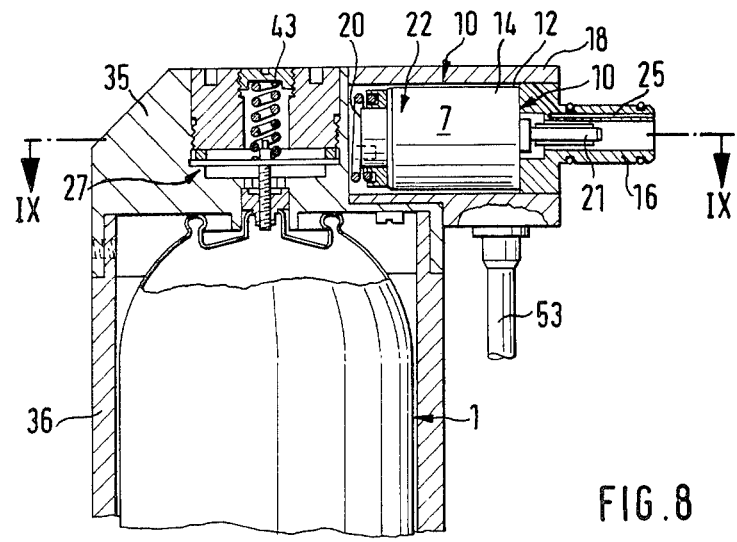
FIG. 8 is a section through a further modified embodiment in comparison with FIG. 2 taken along line VIII—VIII in FIG. 9.
Figure 9:
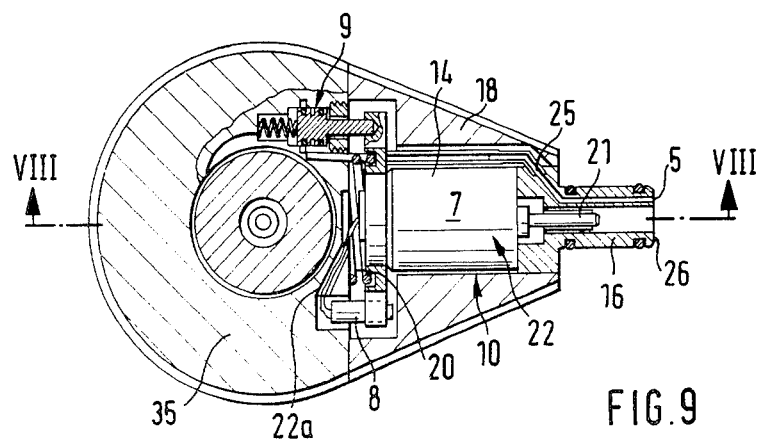
FIG. 9 shows a section taken along the line IX—IX in FIG. 8.

In the embodiments according to FIGS. 1 through 5 and 7, the pressure element 12 consists of a finger-actuatable pressure button 13, whereas in the embodiments pursuant to FIGS. 8 and 9 the pressure element 12 is formed by a pressure element 14 actuatable upon the attachment of the handpiece inlet opening 6 to the receptacle dispensing opening 5.

Figure 6:
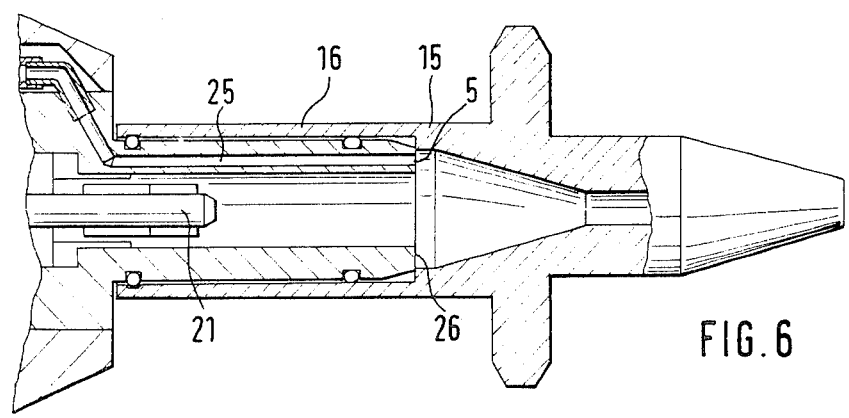
FIG. 6 illustrates an enlarged view of the region of the dispensing opening of the arrangement, for example, in accordance with FIG. 1.

Furthermore, from FIGS. 8 and 9 there may be ascertained that the pressure element 14 is arranged reciprocably within a tubular connector 18 which is in communication with a connector sleeve 16 having the receptacle dispensing opening 5, forming a socket plug element for handpiece 3 or forming an adapter sleeve 15. The adapter sleeve 15, of which an exemplary embodiment is illustrated in FIG. 6, comes into utility in the instances wherein there must be effected a correlation with the specially dimensioned inlet opening of the handpiece, for example, a turbine handpiece. Associated with the pressure element 14 is a return spring 20 which moves the pressure member, after removal of the handpiece 3 which is applied under pressure to the dispensing opening 5, back into the inactive position corresponding to the inoperative position of the two power sources.

From the drawings there can be ascertained that the receptacle 1 is formed by a spray container, and the pressure drive 4 is formed by the internal pressure of the spray container which contains the maintenance medium and a drive medium, wherein the pressure drive switch element 9 consists of a closure valve 17 which includes a closure member 19 movable against the action of the spring 11 into the open position.

Furthermore, the drawings illustrates the motion drive 7 is formed by an electromotor 22 driving the rotary follower 21 upon the attachment of the handpiece 3, with a rotatable work tool drive shaft 2 of the handpiece 3 engageable therewith, wherein the motion drive switch element 8 consists of an electrical switch 23. In the embodiment pursuant to FIGS. 8 and 9, the electromotor 22 forms the pressure element 14 representing the common actuating element 10. The electrical switch 23 posesses a switch rod 24 which is movable by means of the actuating element 10 against the action of a spring (not shown) located in the switch housing into the actuating position. After the depression of the switch rod 24, upon further pressure being exerted upon the pressure button 13 (refer to FIG. 7), the valve rod 19a will move and thereby the valve closure member 19 with the release of the maintenance medium for flow towards the dispensing opening 5. Upon release of the pressure button 13, initially there is interrupted the maintenance medium out flow and there is then switched off the motion drive 7. The electromotor 22 which forms the motion drive 7 runs constantly at about 20,000 rpm and without disruption. The connecting cable from the switch 23 to the electromotor 22 is designated with reference numeral 22a.

The mentioned rotary follower 21 is arranged in the connector sleeve 16. The embodiment according to FIG. 2 has the dispensing opening 5 connecting with the inner space of the connector sleeve 16, whereas in the embodiments according to FIGS. 6 and 8 through 10 the rotary follower 21 and the dispensing opening 5 of the receptacle 1 are arranged spatially separated from each other, whereby an excess moistening, for example, oiling, of the connector sleeve 16 can be prevented. For this purpose, pursuant to FIGS. 6, 8 and 9 there is arranged an outlet conduit 25 in the wall of the connector sleeve 15 leading to the dispensing opening 5 of the receptacle 1 from the pressure drive switch element 9, in which the dispensing opening 5 terminates in the annular end surface 26 of the connector sleeve 16. The outlet conduit, in a manner which is not illustrated herein, can also extend as a separate conduit within the interior of the connector sleeve 16. Pursuant to FIG. 10, the outlet conduit 25 is formed as an annual passageway. For this purpose there can be also arranged two tubular sleeves concentrically within each other, and which sleeves are spaced from each other.

In particular, when in a receptacle 1 which is formed by a spray container there is contained a drive medium which at an increasing degree of emptying will reduce in pressure, for example air, nitrogen or the like, then the spraying of the maintenance medium will, due to the exceedingly low internal pressure, already exhaust at a partially emptied receptacle. In order to avoid this condition, a pressure regulator 27 is associated with the pressure drive 4 which will maintain the internal pressure within the receptacle, at a reducing pressure of the drive medium, constant or generally constant, and which regulator is arranged in the outlet conduit 28 leading from the inner space of the receptacle 1 to the closure valve 17. From FIG. 7 there can further be clearly ascertained that the pressure regulator 27 includes a membrane chamber 29 which is in communication with the inner space of the receptacle 1 as well as with the closure valve 17, whose membrane 30 at the side of the container facing away from the interior space thereof is loaded by a pressure spring 31 acting against the internal pressure of the receptacle 1. The spring force of the spring 31 can be adjusted by rotation of a set screw 43, as is ascertainable in FIGS. 2 and 8.

As is further illustrated in FIG. 7, the pressure regulator 27 is in communication at one end thereof with a transfer rod 44 which is fastened to the membrane 30, and at its other end to a bell-shaped switch cap 45 connected with the last mentioned, connected with a stop element 32 responsive at a minimum internal pressure of the receptacle 1, or an empty receptacle, which is formed through an optical display element 33, for example, an electrical lamp and/or latching element 34 movable in the actuating path of the pressure element 12 of the closure valve 17. Upon a dropping of the internal pressure of the receptacle 1, the membrane 30 will bend inwardly under the effect of the spring 31, in effect, downwardly in FIG. 7, so that the switch cap 45 is pulled downwardly on with its lower edge will actuate a switch 46 associated with the lamp 33; in essence, a sphere forming the latching element 34 slides below the lower edge of the hood-shape constructed pressure element 12. For the last mentioned purpose, the lower edge of the switching cap 45 includes a reduction 47 causing displacement of the sphere 34 in FIG. 7 towards the right.

The closure valve 17 which forms the switch element 9 of the pressure drive power source is arranged in a mounting block 35 attachable on the receptacle 1, which forms the cover of a housing 36 encompassing the receptacle 1, wherein the mounting block 35 also contains the pressure regulator 27.

The electromotor 22 which forms the motion drive 7 is arranged in the wall of a closure 37 supported on the mounting block 35. Pursuant to FIG. 2, the closure cap 37 is provided with a breakthrough closable by cover 49, in order to render the set screw 43 accessible for purpose of adjustment. In the embodiments pursuant to FIGS. 2 and 7 the rotary follower 21 is driven through an angle drive 48 arranged in the wall of the closure cap 37, and in the embodiments pursuant to FIGS. 8 and 9 is driven directly, in effect, coaxially with the motor shaft. It is ascertainable that the pressure button 13 forming the common actuating element 10 passes through the wall of the closure cap 37 and, for rendering readily visible the optical display element 33, is arranged in the wall of the closure cap 37.

Figure 11:
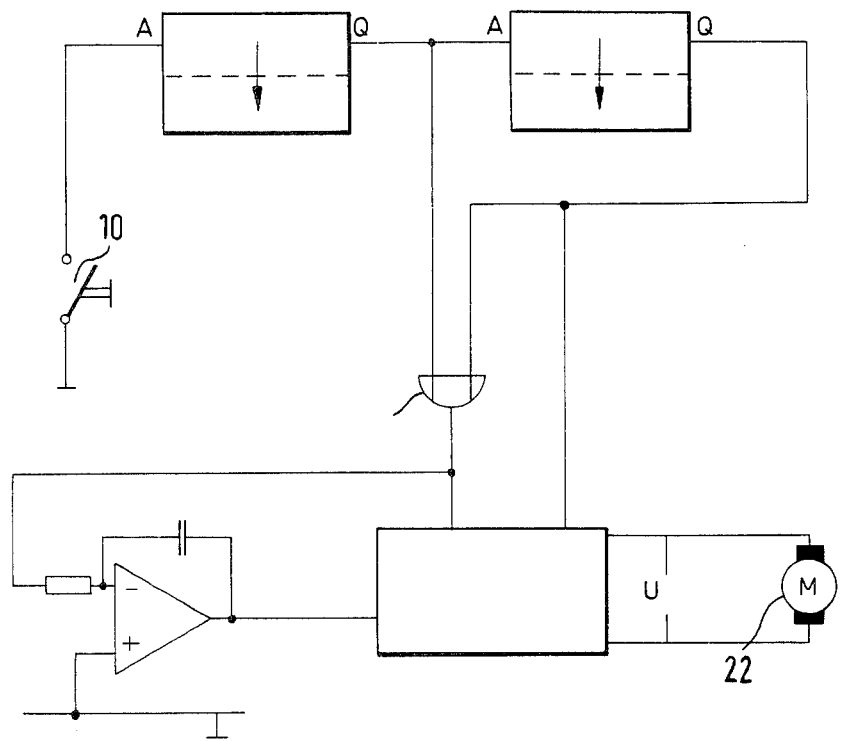
FIG. 11 is en electrical circuit diagram of an interval circuit for a sequentially following right-left run of an electromotor forming a motion drive for the arrangement.
Figure 12:
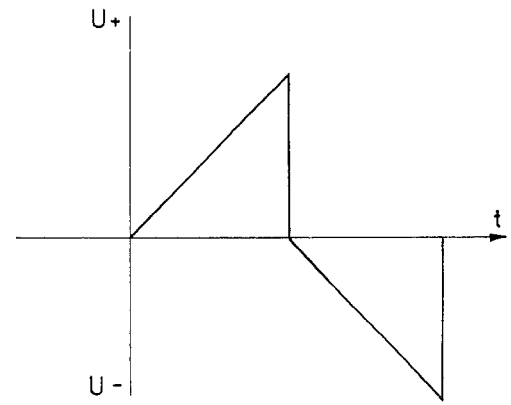
FIG. 12 graphically illustrates the currently smooth acceleration of the right-left run of the electromotor.

Instead of being encompassed by a housing 36, the receptacle 1 according to FIG. 1 can be also arranged vertically on a pedestal plate 50 and detachably fastened by means of bayonet closure 51. From the pedestal plate 50, at the sides adjacent the receptacle, two retaining rods 52 extend upwardly and are connectable with the closure cap 37 which, in addition, includes an electrical connecting cable 53 below the electromotor 22. On the upper side of the edge 54 of the pedestal plate 50 projecting sideways above the receptacle 1 there are also arranged plug pins 55 as retainers for further handpieces 3 or adapter sleeves 15. The electromotor 22 which forms the motion drive 7 has associated therewith a circuit effecting a timed sequential clockwise rotation and counterclockwise rotation of the motor. This circuit which represents an interval circuit, is illustrated in FIG. 11 wherein out designates the output voltage, and "A" the input as well as "Q" the output. FIG. 12 illustrates the presently smooth acceleration of the clockwise or counterclockwise rotation of the electromotor 22, plotted over the time period t.

Figure 10:
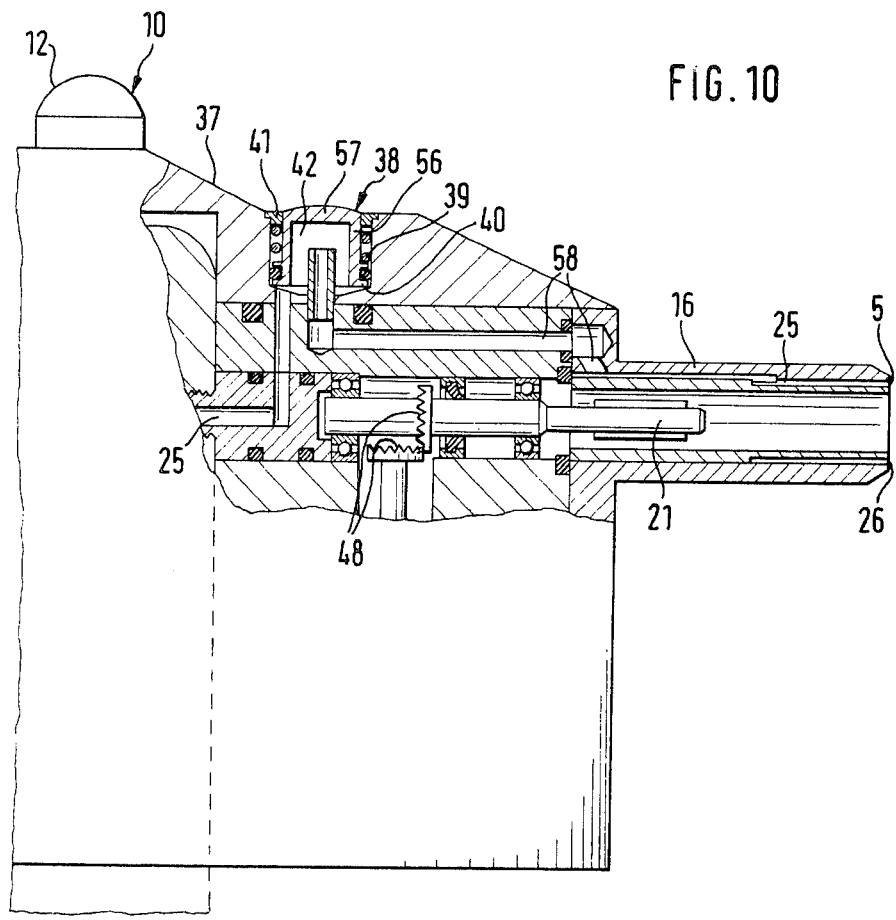
FIG. 10 is a further modified embodiment in comparison with that of FIG. 2 shown in an enlarged scale.

In order to ensure that no handpieces 3 will be further attached to the dispersing opening 5 by a user, and that the actuating element 10, which for the remainder can be constructed in the type of a key switch, is actuated when within the receptacle 1, which is generally constituted of opaque material, has no longer any maintenance medium therein, according to FIG. 10 the outlet conduit 25 which leads to the dispensing opening 5 has a viewing element 38 therein indicating the through flow of the maintenance medium. The viewing element 38, in a manner not shown herein, can be arranged in the mounting block 35 or, pursuant to FIG. 10, in the the wall of the closure cap 37. The viewing element 38 is further constructed as an outwardly protruding pressure knob under pressure from the outlet conduit 25 out of the mounting block 35 or from the wall of the closure cap 37 into the display position. Hereby, the viewing knob has a return spring 39 associated therewith which holds the same with a non-pressurized outlet conduit 25 in the non-display position, which spring has one end thereof contacting against the projection 40 of the viewing element 38 and with its other end against a stop 41 on the mounting block 35, or which lies against the closure cap 37. As may be further ascertained from FIG. 10, the outlet conduit 25 includes a branch conduit 42 which communicates with the exterior, which is closed off by the viewing element 38. The viewing element is formed as a hood-like cylindrical viewing glass whose side walls 56 are located within the branch conduit 42 and whose hood bottom 57 in the non-indicating position thereof is essentially closely engaged with the outer wall of the closure cap 37. From the interior of the hood, or from the interior of the branch conduit 42, an intermediate conduit 58 leads to the portion of the outlet conduit 25 leading further to the dispensing opening 5.

Figure 13:
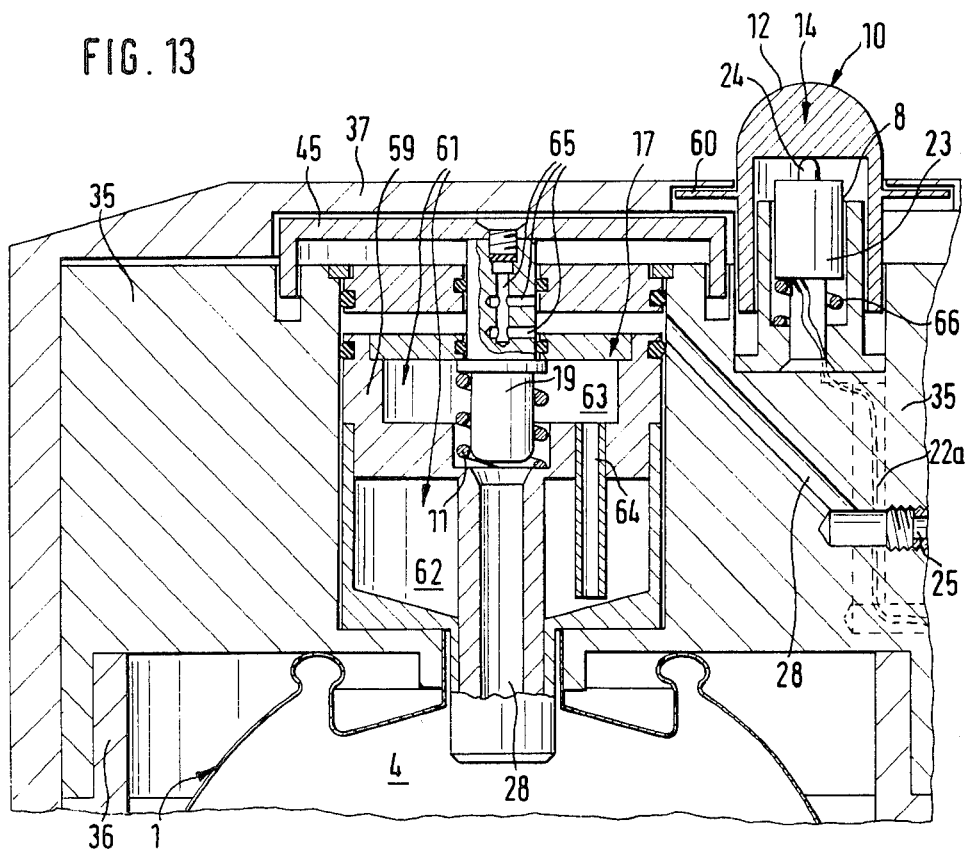
FIG. 13 is a further embodiment of the invention modified in comparison with FIG. 2, shown in an enlarged scale.

In order to facilitate the dispensing of an optimum quantity of maintenance medium, which is precisely correlated with the current purpose of use, for example, the maintenance of turbine handpieces, electromotor handpieces or the like, pursuant to FIG. 13 the dispensing opening 5 of the receptacle 1 has associated therewith a metering valve which upon its actuation dispenses a predetermined quantity of maintenance medium. Suitable the metering valve 59 forms the closure rod 17. FIG. 13 further illustrates that the closure member 19 of the closure valve 59 is movable through a follower 60 of the actuating element 10 in opposition to the action of the spring 11 into the open position wherein the one metering chamber 61 of the metering valve is brought into communication with the portion of the outlet conduit 28 leading towards the dispensing opening 5, in which there is interrupted the connection of the metering chamber 61 with the interior space of the receptacle 1. Through the arrangement of the metering valve 59 there is prevented an excess flow of maintenance medium, for example, in the form of excessive oiling, to the handpices 3. Furthermore, the metering valve 59 provides the advantage that the circuit causing a following of the motion drive 17 after termination of the pressure drive 4 is simplified or, in essence, can be completely eliminated, since depression of the pressure element 14 initially causes the switch rod 24 to actuate the switch element 8 and, thereby, the motion drive 7 is set into operation,; only thereafter by means of the annular-like follower 60 is the valve closure member 19 which has the through passageways 65 brought into the open position, whereby the receptacle 1 having the metering chamber 61 formed by two chamber 63 and 62 connected by a riser tube 64, has the metered maintenance medium quantity contained therein dispensed through the dispensing opening 5. When the pressure element 14 is then held depressed, the motion drive 7 will run until the termination of the depressing action; however, with the advantage that during this further depressing no maintenance medium can be dispensed.

Upon the depressing of the pressure element 14 there is initially pressed in the switch rod 24 of the electrical switch 23 forming the power sources switch element 8 of the electromotor 22, and hereby through the connecting cable 22a the current circuit of the electromotor is closed and the last-mentioned is set into operation. The further depressing of the pressure member 14 is effecting against the action of a pressure spring 66 acting from below against the switch 23 and serving as a resetting element, until the follower 60 comes into contact with a transfer element of the valve closure body 19 which is formed as the switch bell cap 45, and the latter, as mentioned is moved into the open position.

Naturally, subsequent to the termination of the depressing action, the described sequence can be repeated.

What is claimed is:

1. In an arrangement for the dispensing from a receptacle of pressurizable cleaning and lubricating media constituting maintenance media to movable components retaining medical, and particularly dental handpieces; including a pressure drive forcing the maintenance medium from a dispensing opening of said receptacle through an inlet opening of a handpiece attached to the dispensing opening; and a motion drive for setting the movable components into motion during the forcing in of the maintenance medium; the improvement comprising: separate power sources being associated with respectively said motion drive and said pressure drive; separate switch elements for activating and deactivating respectively said motion drive power source and said pressure drive power source; a common actuating element being operatively associated with said separate switch elements, said common actuating element actuating said motion drive power source prior to actuating said pressure drive power source, said common actuating element comprising a pressure element, said pressure element comprising a pressure member actuatable upon the attachment of the handpiece inlet opening to the receptacle dispensing opening, a connector conduit for reciprocably receiving said pressure member, said conduit communicating with a connecting sleeve having said receptacle dispensing opening, said connecting sleeve forming a mounting means for said handpiece, and switch elements being movable into a switched position corresponding to one of the operating positions of said power sources; and spring means acting on said common actuating element to exert a biasing force thereon opposite the motion of said switch elements.

* * * * *